(12) United States Patent
Jacobs et al.

(10) Patent No.: US 6,676,700 B1
(45) Date of Patent: Jan. 13, 2004

(54) STENT WITH RADIOPAQUE CORE

(75) Inventors: James M. Jacobs, Mountain View, CA (US); Ryan John Santos, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 236 days.

(21) Appl. No.: 10/002,715

(22) Filed: Nov. 1, 2001

Related U.S. Application Data

(62) Division of application No. 09/416,879, filed on Oct. 13, 1999, now Pat. No. 6,387,123.

(51) Int. Cl.⁷ .................................................. A61F 2/06
(52) U.S. Cl. ...................................... 623/1.34; 623/1.44
(58) Field of Search .............................. 623/1.34, 1.44, 623/1.46, 1.35, 1.2, 1.13; 606/191, 195, 198

(56) References Cited

U.S. PATENT DOCUMENTS

| | | | |
|---|---|---|---|
| 5,282,823 A | 2/1994 | Schwartz et al. | |
| 5,314,444 A | * 5/1994 | Gianturco | 606/195 |
| 5,464,438 A | 11/1995 | Menaker | |
| 5,607,442 A | 3/1997 | Fischell et al. | |
| 5,609,629 A | * 3/1997 | Fearnot et al. | 623/1.34 |
| 5,628,787 A | 5/1997 | Mayer | |
| 5,629,077 A | 5/1997 | Turnlund et al. | |
| 5,645,559 A | 7/1997 | Hachtman et al. | |
| 5,667,523 A | 9/1997 | Bynon et al. | |
| 5,723,004 A | 3/1998 | Dereume et al. | |
| 5,725,570 A | 3/1998 | Heath | |
| 5,725,572 A | 3/1998 | Lam et al. | |
| 5,843,166 A | 12/1998 | Lentz et al. | |
| 5,858,556 A | 1/1999 | Eckert et al. | |
| 6,174,329 B1 | 1/2001 | Callol et al. | |

* cited by examiner

*Primary Examiner*—Kevin T. Truong
(74) *Attorney, Agent, or Firm*—Fulwider Patton Lee & Utecht, LLP

(57) ABSTRACT

A stent configuration wherein a radiopaque material is completely encapsulated in a skin of biocompatible material to prevent the exposure of radiopaque materials to living tissue and to prevent galvanic corrosion between disparate metals. The stent is initially formed and rendered radiopaque after which all surfaces are coated with the biocompatible material.

12 Claims, 2 Drawing Sheets

STENT WITH RADIOPAQUE CORE

This is a divisional application of application Ser. No. 09/416,879, filed Oct. 13, 1999, now U.S. Pat. No. 6,387,123 the contents of which are hereby incorporated by reference.

BACKGROUND OF THE INVENTION

The present invention generally relates to endoprosthesis devices, most often referred to as stents, and more particularly pertains to the radiopaque marking of such devices.

Stents or expandable grafts are implanted in a variety of body lumens in an effort to maintain their patency and are especially well-suited for the treatment of atherosclerotic stenoses in blood vessels. These devices are typically implanted by use of a catheter which is inserted at an easily accessible location and then advanced through the vasculature to the deployment site. The stent is initially maintained in a radially compressed or collapsed state to enable it to be maneuvered through the lumen. Once in position, the stent is deployed which, depending upon its construction, is achieved either automatically by for example the removal of a restraint, or actively by for example the inflation of a balloon about which the stent is carried on the deployment catheter.

The stent must be able to simultaneously satisfy a number of mechanical requirements. First and foremost, the stent must be capable of withstanding the structural loads that are imposed thereon as it supports the lumen walls. In addition to having adequate radial strength or more accurately, hoop strength, the stent should nonetheless be longitudinally flexible to allow it to be maneuvered through a tortuous vascular path and to enable it to conform to a deployment site that may not be linear or may be subject to flexure. The material of which the stent is constructed must allow the stent to undergo expansion which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

Fluoroscopy has typically been relied upon to facilitate the precise placement of a stent as well as to verify the position of a stent within a patient throughout its service life. The use of radiopaque materials in the construction of the stent allows for its direct visualization. Unfortunately, no single material to date has been identified that simultaneously satisfies all requirements inherent in a stent application. Those materials that do satisfy the mechanical requirements are either insufficiently or excessively radiopaque and/or have not been adequately proven to be biocompatible in a vascular setting. Thus, simply constructing a radiopaque stent wholly out of a single material is to date not a viable option. A number of different approaches, however, have been employed wherein different materials are combined in an effort to render a mechanically sound and biocompatible stent to be fluoroscopically visible.

One means frequently described for accomplishing flouroscopic visibility is the physical attachment of radiopaque markers to the stent. Conventional radiopaque markers, however, have a number of limitations. Upon attachment to a stent, such markers may project from the surface of the stent, thereby comprising a departure from the ideal profile of the stent. Depending on their specific location, the marker may either project inwardly to disrupt blood flow or outwardly to traumatize the walls of the blood vessel. Additionally, the galvanic corrosion that might result from the contact of two disparate metals, i.e., the metal used in the construction of the stent and the radiopaque metal of the marker could eventually cause the marker to become separated from the stent which could be problematic should the marker be swept downstream. Finally, although the such markers are typically fairly small, this approach does cause the radiopaque material to come into direct contact with living tissue which may be problematic should there be any biocompatibility issues.

Stents also have been previously marked by plating selected portions thereof with radiopaque material. However, a number of disadvantages are associated with this approach as well. This again causes the radiopaque material to come into direct contact with living tissue which, depending on the total area that is plated, can amount to a sizeable exposure. Additionally, when the stent is expanded and certain portions thereof are caused to undergo substantial deformation, there is a risk that cracks would form in the plating and that sections thereof would become separated from the underlying substrate. This has the potential for creating jagged edges that may inflict physical trauma on the wall tissue or cause turbulence in the blood flowing thereover to thereby induce thrombogenesis. Moreover, once the underlying structural material becomes exposed, interfaces between the two disparate metals become subject to galvanic corrosion. Further, should the plating pattern cover less than all of the stent's surfaces, the margins between the plated and unplated regions all are subject to galvanic corrosion.

As a further alternative, a stent structure has been described that is formed from a sandwich of structural and radiopaque materials. Three tubes of the materials are codrawn and heat treated to create a structural/radiopaque/structural materials sandwich. Struts and spines are then formed in the tube by cutting an appropriate pattern of voids into the tube as is well known in the art. While this approach does provide a stent that is radiopaque and that fulfills the necessary mechanical requirements, the thin cross section of the radiopaque material is nonetheless exposed along the edges of all cut lines. The biocompatiblity of the radiopaque material therefore remains an issue and more significantly, a sizeable area is thereby created that is subject to galvanic corrosion. Any cuts in the sandwich structure cause two disparate metal interfaces, i.e., the juncture between the outer structural layer and the central radiopaque layer as well the juncture between the central radiopaque layer and the inner structural layer, to become exposed along the entire lengths of such cuts.

A stent configuration is therefore required that overcomes the shortcomings inherent in previously known devices. More specifically, a stent structure is needed that provides the requisite mechanical properties for such application, that exposes only fully biocompatible materials to living tissue and that is fluoroscopically visible.

SUMMARY OF THE INVENTION

The present invention provides a stent that overcomes the shortcomings of previously known stent devices. The stent fulfills all of the mechanical and structural requirements attendant to its function as a stent. Moreover the stent is fluoroscopically visible without any radiopaque material being exposed to living tissue and without any disparate metal interfaces being subject to galvanic corrosion.

The advantages of the present invention are achieved with the complete encapsulation of all radiopaque material that is associated with the stent. In one embodiment a substantially conventional stent is first formed of a structural material by any one of a number of conventional methods. Radiopaque material is then applied to the structure to cover all or just selected portions thereof. A fully biocompatible material is then applied to all surfaces. By fully encapsulating the underlying radiopaque material, any biocompatiblity issues related to the radiopaque material are effectively eliminated as is the potential for galvanic corrosion. Additionally, by ensuring that the outer encapsulating biocompatible skin (or layer) is of sufficient thickness and strength, the risk of compromising the integrity of the skin during the severe deformation that portions of the stent undergo during expansion is also substantially eliminated. Additionally, the outer skin may also be relied upon to contribute to the overall mechanical strength of the stent.

In an alternative embodiment, the underlying stent structure is formed of a radiopaque material that has some or all of the required mechanical properties but may not have been proven to be fully biocompatible in a vascular setting. A structural material that is fully biocompatible is then applied thereto to not only preclude contact between the underlying material and living tissue but to additionally contribute to the mechanical properties of the stent. By fully encapsulating the underlying material, no disparate metal interfaces are exposed to galvanic corrosion.

The radiopaque material may be applied to the underlying structural material by employing any one of a number of well known techniques which include, but are not limited to electroplating, electroless plating, co-drawing and sputter coating. The radiopaque material may be applied to all surfaces of the underlying structure or may be selectively applied so as to form preselected patterns thereon. By advantageously selecting such patterns, the precise orientation or the degree of expansion of the stent may be discernible upon fluoroscopic illumination.

The outer encapsulating skin (or layer) similarly may be applied by any one of the many well known techniques. The material selected for use will usually dictate which method is best suited for its application. Finally, the radiopaque and fully encapsulated stent is subjected to an annealing step wherein an elevated temperature is maintained for a preselected period of time. This serves to enhance the strength of the applied layers and to form strong bonds therebetween.

These and other features and advantages of the present invention will become apparent from the following detailed description of preferred embodiments which, taken in conjunction with the accompanying drawings, illustrate by way of example the principles of the invention.

DETAILED DESCRIPTION OF THE PREFERRED EMBODIMENTS

A stent constructed in accordance with the present invention is employed to maintain the patency of selected body lumens in the conventional manner both in terms of application as well as deployment. The advantages afforded by the stent are inherent in its ability to provide the required strength, to expose only biocompatible materials to living tissue and to preclude the possiblitiy of galvanic corrosion despite the fact that disparate metals are employed in its construction.

Figure 1:
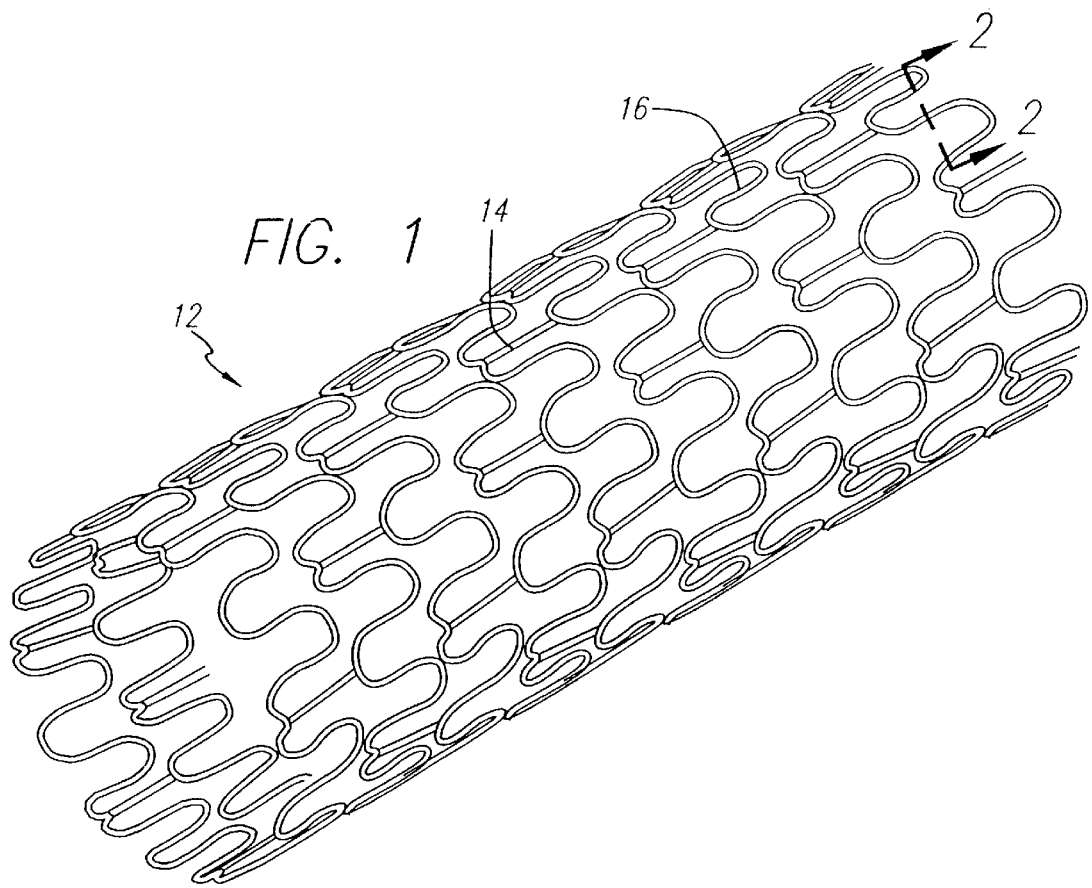
FIG. 1 is a perspective view of a stent of the present invention.

FIG. 1 illustrates a tubular stent 12 constructed in accordance with the present invention. The underlying structure is formed in the conventional manner in that a tube has a carefully preselected pattern of voids formed therein such as by laser cutting, etching, micro-machining or electrical discharge metal removal. The pattern of voids serves to define an intricate network of spines 14 and struts 16 that enable the tube to expand radially when subjected to the appropriate radially directed forces such as are exerted by the inflation of an underlying balloon. A myriad of strut and spine patterns are known for achieving various design goals such as enhancing strength, maximizing the expansion ratio, or coverage area, enhancing longitudinal flexibility or longitudinal stability upon expansion, etc. One pattern is selected over another in an effort to optimize those parameters that are of particular importance for a particular application.

Figure 2:
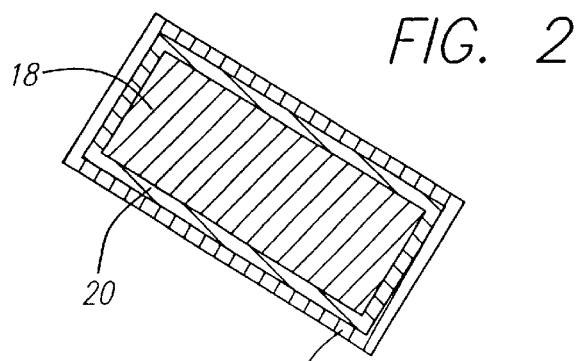
FIG. 2 is a greatly enlarged cross-sectional view taken along lines 2—2 of FIG. 1 illustrating a preferred embodiment of the present invention.

FIG. 2 is a cross-sectional view of the stent of the present invention and more specifically, is the cross-section of a single strut 16. Visible in the illustration are a total of three elements which include a central core 18, an intermediate coating 20, and an encapsulating skin (or layer) 22. The central core 18 in fact comprises the underlying structure of the stent that is formed in the manner described above and defines the overall configuration of the stent. The material employed for such underlying structure is selected for its structural and mechanical properties and may in fact be the same material of which conventional stents are exclusively formed. Suitable materials include, but are not limited to nickel-titanium, cobalt-based alloys, Nitinol and stainless steel. Stainless steel and more specifically the 316L alloy is preferred. Such materials when used in the 0.002" to 0.003" thickness that is typical for stent applications are substantially fluoroscopically transparent.

The material used in the intermediate coating 20 is selected for its radiopacity. Appropriate materials include but are not limited to gold, silver, platinum, tantalum, iridium or their alloys. Such materials are highly visible under fluoroscopic illumination and are therefore visible even at very minimal thicknesses. Their mechanical properties, and more specifically their low strength and high malleability, preclude their exclusive use in the construction of a stent. Moreover, if such materials were to be used in sufficient thicknesses to afford the requisite strengths, they would typically illuminate so brightly so as to obscure the deployment site and preclude visualization of features in the lumen wall. Accurate positioning of the stent would therefore be rendered difficult at best. Finally, although many of the above listed radiopaque materials have been used in the human body for some time, their long-term effect in a vascular setting may or may not have been established.

The material employed in the outer skin 22 is one the biocompatability of which in a vascular setting has been firmly established. Appropriate materials include but are not limited to nickel-titanium, cobalt-based alloys, Nitinol and stainless steel. Stainless steel, namely the 316L alloy is again preferred. The material employed in the central core 18 and the outer encapsulating skin 22 may or may not be the same. The material for the outer skin may additionally be selected for its ability to contribute to the overall strength of the resulting stent.

In manufacturing a stent as is illustrated in FIG. 1, and more particularly in FIG. 2, a tube of 316L stainless steel tubing having a wall thickness of 0.0028" is first laser cut to provide a desired pattern of voids defining struts and spines, all in accordance with well known and well established procedures. After the voids have been cut into the tube, the surfaces of the cut tubing are electropolished to provide an extremely smooth surface. This again comprises a well known technique wherein the workpiece is immersed in a phosphoric acid based solution and subjected to an electric potential. In the treatment of stainless steel, the procedure not only serves to smooth out the surface, but additionally serves to remove iron from near the surface to leave behind a chromium-rich stratum with enhanced corrosion resistance. The stent core preferably is subjected to the electropolishing step for a period of time sufficient to reduce the wall thickness of the stainless steel core from its initial 0.0028" to 0.0022". Alternatively, bead blasting or microsanding may be employed to achieve a sufficiently smooth surface.

The radiopaque coating 20 is subsequently applied to the electropolished core 18. One preferred material is gold and the preferred method of application is sputter coating which comprises another well known technique. The applied material is melted, atomized, electrically charged and accelerated toward the stent workpiece with the application of the appropriate voltage differentials. Sputter coating machines are commercially available that are capable of applying an extremely even coating of material to a workpiece. The workpiece may be rotated in front of a target, the target may be rotated about the workpiece or a target that completely surrounds the workpiece may be employed to apply the sputter coating. The gold is preferably applied to a thickness of 0.00014" to bring the total wall thickness of the stent structure to 0.00248". The radiopaque coating may be applied to the entire stent structure or to only selected portions thereof by for example the use of masks. Advantageously selected patterns of radiopacity allow the precise orientation or degree of expansion to be discerned by inspection of the fluoroscopic image. Alternatively, the gold may be applied by electroplating, vacuum deposition, or electroless plating. As a further alternative, gold tubing may be codrawn with stainless steel tubing to yield a stainless steel/gold composite structure which is then laser cut to form voids therein. Other preferred materials for coating 20 includes platinum, iridium, and tantalum.

The outer encapsulating skin 22 is subsequently applied to the gold coated stainless steel core. The preferred material is 316L stainless steel, and the preferred method of coating is again by sputter coating. The stainless steel is applied to a thickness of 0.000020" to bring the total wall thickness of the stent to 0.00252".

In a final step, the coated structure is annealed by maintaining the stent at an elevated temprature for a period of time. The upper limit of these conditions is dictated by the diffusion rate of the gold. Diffusion to the surface must of course be prevented in order to preclude the biocompatiblity or galvanic corrosion problems that encapsulation seeks to obviate. Annealing conditions that have been found to be preferable for the stainless steel/gold/stainless steel structure of the dimensions described above have been found to comprise raising the temperature of the stent to 800°–1300° C. and maintaining such temperature for two to fifteen minutes. In addition to forming positive bonds between the disparate materials, annealing also has the desireable effect of creating a grain structure within the applied metal coatings, especially within the outer skin, which then serves to enhance the overall strength of the stent.

In an alternative embodiment, a laser cut tube of 316L stainless having a wall thickness of 0.0028", first is electropolished down to 0.0017". A 0.00014" thick coating of gold is then applied thereover by sputter coating followed by the application of an outer skin of 316L stainless steel to a depth of 0.00031". This yields a total wall thickness of 0.0026" which is then electropolished down to 0.0022". During the electropolishing step, only the stainless steel layers are chemically polished. The coated and polished stent is then annealed at a temperature of 800°–1300° C. for a period of two to fifteen minutes.

Figure 3:
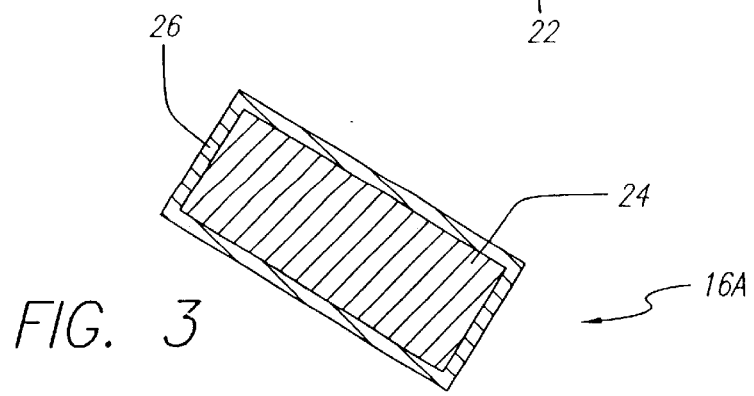
FIG. 3 is a greatly enlarged cross-sectional view similar to that shown in FIG. 2 but of an alternative embodiment of the present invention.

FIG. 3 illustrates an alternative embodiment of the present invention wherein the stent core 24 has a single coating 26 applied thereto. In such embodiment, the core 24 is composed of a material that has both the desired structural properties as well as the desired radiopacity. Such materials include for example a platinum-palladium-nickel alloy or nickel-titanium alloy. After the underlying stent structure is formed of such material and electropolished in a manner similar to that described above, an encapsulating skin 26 of stainless steel is sputter coated thereover. By increasing the depth of the outer skin 26, relative to the thickness of the core 24, such skin can be relied upon for a more substantial contribution to the total strength of the resulting stent The stents of the present invention can be formed by any of a number of well known methosd such as laser cutting a pattern in a tube, chemical etching a pattern in tube, and electron discharge machining (EDM) a pattern in a tube. Each of these methods also can be used to form a stent pattern in a flat sheet which is then rolled into a cylinder and a longitudinal weld attaches the longitudinal edges of the stent. All such stent processes require electropolishing, which is well known, to remove processing impurities and form a smooth stent surface. It is contemplated that the various layers of radiopaque materials preferably are added before the laser cutting or chemical or EDM etching steps which form the stent pattern.

Figure 4:
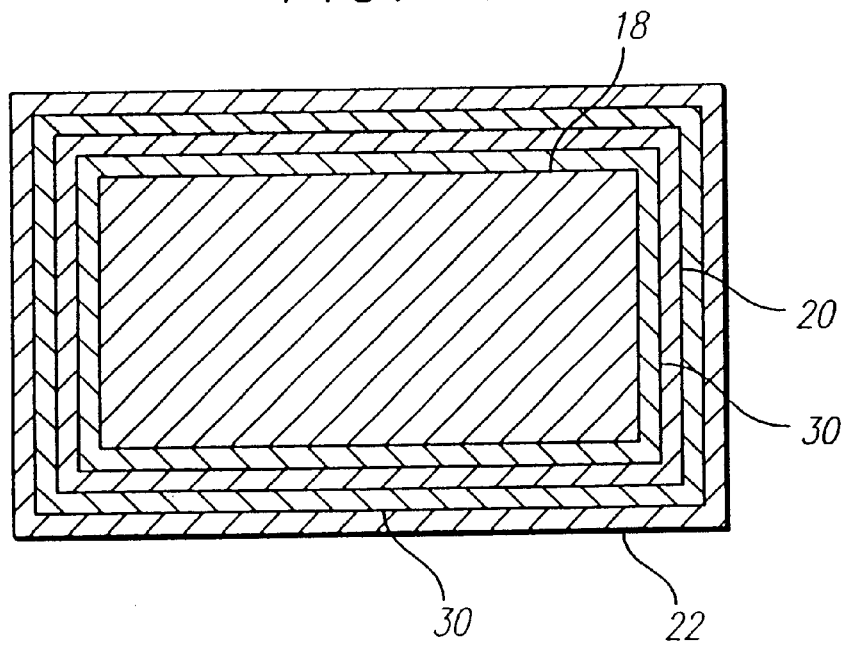
FIG. 4 is a greatly enlarged cross-sectional view similar to that shown in FIG. 2, but of an alternative embodiment of the present invention.
Figure 5:
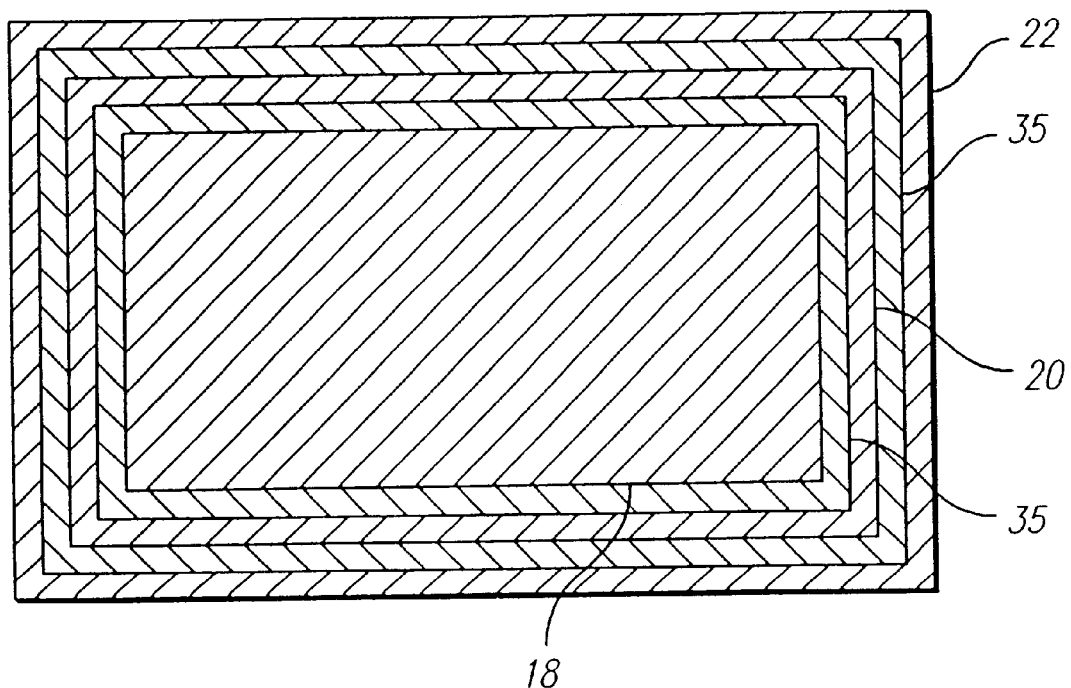
FIG. 5 is a greatly enlarged cross-sectional view similar to that shown in FIG. 2, but of an alternative embodiment of the present invention.

In keeping with the invention, as shown in FIG. 4 adhesion layer 30 preferably is applied between both the central core 18 and coating 20 as well as between coating 20 and outer skin 22 to promote adhesion between the layers. Adhesion between layers is especially important due to stent expansion and the dynamic environment in which the stent is implanted, which may promote delamination between layers.

The invention also includes diffusion layers or barriers to inhibit mixing or diffusion of the elements of the various materials. As shown in FIG. 4, diffusion barriers 35 are applied between the various metal surfaces including between core 18 and coating 20, and between coating 20 and skin 22.

While a particular form of the invention has been illustrated and described, it will also be apparent to those skilled in the art that various modifications can be made without departing from the spirit and scope of the invention. More specifically, it should be clear that the present invention is not limited to tubular type stents nor is it limited to any particular method of forming the underlying stent structure. Additionally, the invention is not limited to the use of any particular materials in either the core, radiopaque coating or encapsulating skin nor is it intended to be limited to any particular coating or application method. Accordingly, it is not intended that the invention be limited except by the appended claims.

What is claimed:

1. A method for forming a radiopaque stent, comprising the steps of:

providing a tube of structural material;

forming voids in said tube to render said tube expandable;

coating said expandable tube with a radiopaque material;

completely encapsulating all surfaces of said coated tube with a layer of biocompatible material; and annealing said encapsulated tube to create grain structure in at least said layer of biocompatible material.

2. The method of claim 1, further comprising the step of annealing the coated and encapsulated tube at a temperature of approximately 800°–1300 degrees C. for a period of approximately two to fifteen minutes.

3. The method of claim 1, further comprising the step of electopolishing said expandable tube prior to said coating and encapsulation steps.

4. The method of claim 1, wherein said voids are formed in said tube by laser cutting.

5. The method of claim 1, wherein said radiopaque coating is applied to said expandable tube by any of sputter coating, electroplating, electroless plating, and vacuum deposition.

6. The method of claim 1, wherein said radiopaque coating is applied to all portions of said expandable tube.

7. The method of claim 1, wherein said radiopaque coating is applied to only selected portions of said expandable tube.

8. The method of claim 1, wherein said layer of biocompatible material is applied by any of sputter coating, electroplating, electroless plating, and vacuum deposition.

9. A method for forming a radiopaque stent, comprising the steps of:

providing a tube of stainless steel;

forming voids in said tube by laser cutting to render said tube expandable;

electropolishing said expandable tube;

sputter coating said electropolished tube with gold;

completely encapsulating said gold coated tube with a sputter coated layer of stainless steel; and annealing said encapsulated stent to create grain structure in at least said layer of biocompatible material.

10. The method of claim 9, further comprising the step of electropolishing said encapsulated stent prior to said annealing step.

11. A method for forming a radiopaque stent, comprising:

providing a tube of structural material including a nickel-titanium alloy;

forming voids in said tube to render said tube expandable;

coating said expandable tube with a radiopaque material;

completely encapsulating all surfaces of said coated tube with a layer of biocompatible material; and annealing said encapsulated tube to create grain structure in at least said layer of biocompatible material.

12. The method of claim 11, wherein said biocompatible material is selected from the group consisting of nickel-titanium alloys, cobalt-based alloys, or stainless steel.

* * * * *